United States Patent
Higuchi et al.

(10) Patent No.: US 7,042,488 B2
(45) Date of Patent: May 9, 2006

(54) ELECTRONIC ENDOSCOPE FOR HIGHLIGHTING BLOOD VESSEL

(75) Inventors: Mitsuru Higuchi, Saitama (JP); Keiichi Negishi, Yokohama (JP); Daisuke Ayame, Saitama (JP); Kazunori Abe, Saitama (JP); Shinji Takeuchi, Saitama (JP)

(73) Assignee: Fujinon Corporation, Saitama (JP)

( * ) Notice: Subject to any disclaimer, the term of this patent is extended or adjusted under 35 U.S.C. 154(b) by 241 days.

(21) Appl. No.: 10/255,080

(22) Filed: Sep. 26, 2002

(65) Prior Publication Data
US 2003/0071895 A1   Apr. 17, 2003

(30) Foreign Application Priority Data
Sep. 27, 2001   (JP)   .............................. 2001-295271
Jan. 30, 2002   (JP)   .............................. 2002-021076

(51) Int. Cl.
*H04N 7/18* (2006.01)
(52) U.S. Cl. .......................................... 348/65; 348/68
(58) Field of Classification Search ............. 348/65–76
See application file for complete search history.

(56) References Cited

U.S. PATENT DOCUMENTS

| | | | |
|---|---|---|---|
| 4,728,591 A | 3/1988 | Clark et al. | |
| 5,106,729 A | 4/1992 | Lindsay et al. | |
| 5,138,174 A | 8/1992 | Tang | |
| 5,143,854 A | 9/1992 | Pirrung et al. | |
| 5,314,829 A | 5/1994 | Coles | |
| 5,346,683 A | 9/1994 | Green et al. | |
| 5,363,697 A | 11/1994 | Nakagawa | |
| 5,372,930 A | 12/1994 | Colton et al. | |
| 5,384,261 A | 1/1995 | Winkler et al. | |
| 5,440,122 A | 8/1995 | Yasutake | |

(Continued)

FOREIGN PATENT DOCUMENTS

JP   06124680   5/1994

(Continued)

OTHER PUBLICATIONS

"Microbeam Mass Spectrometry" *Chemical Science and Technology Laboratory, Surface and Microanalysis Science Division* http://www.cstl.nist.gov/div837/Divisoin/expertise/ions/masspec1.htm Jul. 18, 2002.

(Continued)

*Primary Examiner*—Andy Rao
(74) *Attorney, Agent, or Firm*—Snider & Associates; Ronald R. Snider (57) ABSTRACT

In an electronic endoscope of the present invention, an edge detection circuit detects a down edge section and an up edge section of both ends of a blood vessel in a width direction based on a G signal output from an RGB color conversion circuit, an R coefficient selector and a B coefficient selector select, for example, a coefficient smaller than 1 for the detected down edge section and select, for example, a coefficient larger than 1 for the up edge section, and a multiplier multiplies an R signal and a B signal by these coefficients. As a result, both ends of the blood vessel are highlighted with a left end part expressed blackish and a right end part expressed reddish, making it possible to clearly display blood vessels in mucous membranes on a monitor. It is also possible to detect phases on a coordinate system where an R-Y signal is set on a vertical axis and a B-Y signal is set on a horizontal axis, compare these phases with reference phase $\theta_1$ of blood vessel colors and extract signals of blood vessel colors.

3 Claims, 7 Drawing Sheets

U.S. PATENT DOCUMENTS

| | | | |
|---|---|---|---|
| 5,443,791 A | 8/1995 | Cathcart et al. | |
| 5,445,934 A | 8/1995 | Fodor et al. | |
| 5,445,971 A | 8/1995 | Rohr | |
| 5,453,970 A | 9/1995 | Rust et al. | |
| 5,467,642 A | 11/1995 | Hosaka et al. | |
| 5,472,881 A | 12/1995 | Beebe et al. | |
| 5,482,601 A | 1/1996 | Ohshima et al. | |
| 5,514,540 A | 5/1996 | Teoule et al. | |
| 5,514,550 A | 5/1996 | Findlay et al. | |
| 5,519,212 A | 5/1996 | Elings et al. | |
| 5,532,128 A | 7/1996 | Eggers et al. | |
| 5,550,582 A * | 8/1996 | Takasugi et al. | 348/65 |
| 5,571,639 A | 11/1996 | Hubbell et al. | |
| 5,601,982 A | 2/1997 | Sargent et al. | |
| 5,604,097 A | 2/1997 | Brenner | |
| 5,620,854 A | 4/1997 | Holzrichter et al. | |
| 5,666,190 A | 9/1997 | Quate et al. | |
| 5,670,322 A | 9/1997 | Eggers et al. | |
| 5,688,486 A | 11/1997 | Watson et al. | |
| 5,720,928 A | 2/1998 | Schwartz | |
| 5,744,305 A | 4/1998 | Fodor et al. | |
| 5,753,088 A | 5/1998 | Olk | |
| 5,760,300 A | 6/1998 | Kajimura | |
| 5,763,768 A | 6/1998 | Henderson et al. | |
| 5,789,167 A | 8/1998 | Konrad | |
| 5,800,992 A | 9/1998 | Fodor et al. | |
| 5,837,832 A | 11/1998 | Chee et al. | |
| 5,840,862 A | 11/1998 | Bensimon et al. | |
| 5,846,724 A | 12/1998 | Bensimon et al. | |
| 5,851,769 A | 12/1998 | Gray et al. | |
| 5,866,328 A | 2/1999 | Bensimon et al. | |
| 5,866,434 A | 2/1999 | Massey et al. | |
| 5,874,219 A | 2/1999 | Rava et al. | |
| 5,874,668 A | 2/1999 | Xu et al. | |
| 5,958,701 A | 9/1999 | Green et al. | |
| 5,965,133 A | 10/1999 | Cantor et al. | |
| 5,981,733 A | 11/1999 | Gamble et al. | |
| 5,985,356 A | 11/1999 | Schultz et al. | |
| 5,992,226 A | 11/1999 | Green et al. | |
| 5,993,627 A | 11/1999 | Anderson et al. | |
| 6,004,617 A | 12/1999 | Schultz et al. | |
| 6,024,925 A | 2/2000 | Little et al. | |
| 6,033,911 A | 3/2000 | Schultz et al. | |
| 6,045,671 A | 4/2000 | Wu et al. | |
| 6,080,586 A | 6/2000 | Baldeschwieler et al. | |
| 6,083,763 A | 7/2000 | Balch | |
| 6,087,274 A | 7/2000 | Tonucci et al. | |
| 6,110,426 A | 8/2000 | Shalon et al. | |
| 6,123,819 A | 9/2000 | Peeters | |
| 6,143,574 A | 11/2000 | Karlsson et al. | |
| 6,146,899 A | 11/2000 | Porter et al. | |
| 6,159,742 A | 12/2000 | Lieber et al. | |
| 6,171,797 B1 | 1/2001 | Perbost | |
| 6,180,114 B1 | 1/2001 | Yager | |
| 6,200,737 B1 | 3/2001 | Walt et al. | |
| 6,203,814 B1 | 3/2001 | Fisher et al. | |
| 6,214,552 B1 | 4/2001 | Heroux et al. | |
| 6,218,122 B1 | 4/2001 | Friend et al. | |
| 6,231,744 B1 | 5/2001 | Ying et al. | |
| 6,232,706 B1 | 5/2001 | Dai et al. | |
| 6,239,273 B1 | 5/2001 | Pease et al. | |
| 6,255,469 B1 | 7/2001 | Seeman et al. | |
| 6,270,650 B1 | 8/2001 | Miller | |
| 6,278,231 B1 | 8/2001 | Iwasaki et al. | |
| 6,284,497 B1 | 9/2001 | Sabanayagam et al. | |
| 6,287,850 B1 | 9/2001 | Besemer et al. | |
| 6,289,717 B1 | 9/2001 | Thundat et al. | |
| 6,309,831 B1 | 10/2001 | Goldberg et al. | |
| 6,329,209 B1 | 12/2001 | Wagner et al. | |
| 6,331,396 B1 | 12/2001 | Silverman | |
| 6,350,609 B1 | 2/2002 | Morozov et al. | |
| 6,395,554 B1 | 5/2002 | Regan et al. | |
| 6,406,921 B1 | 6/2002 | Wagner et al. | |
| 6,416,952 B1 | 7/2002 | Pirrung et al. | |
| 6,420,105 B1 | 7/2002 | Landfield et al. | |
| 6,436,647 B1 | 8/2002 | Quate et al. | |
| 6,518,168 B1 | 2/2003 | Clem et al. | |
| 6,573,369 B1 | 6/2003 | Henderson et al. | |
| 6,692,430 B1 * | 2/2004 | Adler | 600/109 |
| 2002/0042081 A1 | 4/2002 | Henderson et al. | |
| 2002/0049375 A1 * | 4/2002 | Strommer et al. | 600/407 |
| 2002/0063212 A1 | 5/2002 | Mirkin et al. | |
| 2002/0076927 A1 | 6/2002 | Henderson et al. | |
| 2002/0114987 A1 | 8/2002 | Oscarsson et al. | |
| 2002/0122873 A1 | 9/2002 | Mirkin et al. | |
| 2002/0123135 A1 | 9/2002 | Henderson et al. | |
| 2002/0146714 A1 | 10/2002 | Lieber et al. | |
| 2002/0172943 A1 | 11/2002 | Henderson et al. | |
| 2002/0179434 A1 | 12/2002 | Dai et al. | |
| 2003/0013111 A1 | 1/2003 | Henderson et al. | |
| 2003/0176768 A1 * | 9/2003 | Gono et al. | 600/109 |

FOREIGN PATENT DOCUMENTS

| | | |
|---|---|---|
| JP | 07027771 | 1/1995 |
| JP | 08094646 | 4/1996 |
| WO | WO 92/15709 | 9/1992 |
| WO | WO 96/31775 | 10/1996 |
| WO | WO 97/06420 | 2/1997 |
| WO | WO 97/18326 | 5/1997 |
| WO | WO 98/05920 | 2/1998 |
| WO | WO 98/18959 | 5/1998 |
| WO | WO 99/31267 | 6/1999 |
| WO | WO 00/04382 | 1/2000 |
| WO | WO 00/04389 | 1/2000 |
| WO | WO 00/04390 | 1/2000 |
| WO | WO 00/36136 | 6/2000 |
| WO | WO 00/41213 | 7/2000 |
| WO | WO 00/46406 | 8/2000 |
| WO | WO 01/60316 | 8/2001 |
| WO | WO 01/918555 | 12/2001 |
| WO | WO 03/001633 | 1/2003 |
| WO | WO 03/36767 | 5/2003 |
| WO | WO 03/038033 | 5/2003 |
| WO | WO 03/048314 | 6/2003 |
| WO | WO 03/052514 | 6/2003 |

OTHER PUBLICATIONS

Abstracts of Papers Part 1, 214th "Abstract 027" *ACS National Meeting American Chemical Society*, Sep. 1997, 2 pgs.

Allison, D., et al., "Direct atomic force microscopy imaging of EcoRI endonuclease site specifically bound to plasmid DNA molecules" *PNAS USA*, 1996, 93:8826-8829.

Allison, D., et al., "Mapping Individual Cosmid DNAs by Direct AFM Imaging" *Genomics*, 1997, 41:379-384.

Alves, et al., Atomic scale imaging of alkanethiolate monolayers at gold surfaces with atomic force microscopy: *J. Am. Chem. Soc.*, Feb. 1992,114(4):1222-1227.

Amro, et al., "Patterning surfaces using tip-directed displacement and self-assembly" *Langmuir*, 2000, 16:3006-3009.

Anwander, et al., "Surface characterization and functionalization of MCM-41 silicas via silazane silylation" *J. Phys. Chem. B.*, 2000, 104:3532-3544.

Arntz, et al., "Label-free protein assay based on a nanomechanical cantilever array" *Nanotechnology*, 14 (2003) 86-90.

Ausubel, F.M., et al. "Current Protocols in Molecular Biology" 1993 ed. vol. 1&2, 1993, Green Publishing Associates and Wiley-Interscience.

Avouris, P., "Engineering Carbon Nanotubes and Nanotube Circuits Using Electrical Breakdown" *Science,* Apr. 2001, 292(5517):706-799.

Bailey, C.P., et al., Cationic oligonucleotides can mediate specific inhibition of gene expression in *Xenopus oocytes Nuc. Acids Res.,* 1998, 26(21):4860-4867.

Bain, et al., "Modeling organic surfaces with self-assembled monolayers" Agnew. Chem. Int. Ed. Engl., 1989, 28(4):506-512.

Baselt, D.R., et al., "A biosensor based on magnetoresistance technology" *Biosens. Bioelectorn,* 1998, 13(7-8):731-739.

Bedouelle, H., "Reagentless fluorescent Immunosensors" *Antibody Engineering,* IBC's 13th International Conference, Dec. 2, 2002.

Belaubre, P. et al., "Fabrication of biological microarrays using microcantilevers" *Applied Physics Letters,.* May 5, 2003, 82(18):3122-3124.

Bensimon, A., et al., "Alignment and sensitive of DNA by a moving interface" *Science,* Sep. 30, 1994; 265(5181):2096-2098 [PMID 7522347] Abstract.

Berggren, et al., "Microlithography by using neutral metastable atoms and self-assembled monolayers" *Science,* Sep. 1995, 269(5228):1255-1257.

Bernard, et al. "Printing patterns of proteins" *Langmuir The ACS Journal of Surfaces and Colliod,* Apr. 1998, 14(9):2225-2229.

Binggeli, et al., "Influence of capillary condensation of water on nanotribology studied by force microscopy" *Appl. Phys. Lett.,* Jul. 1994, 65(4):415-417.

Binning, et al., "Surface studies by scanning tunneling microscopy" *Phys. Rev. Lett.,* 1982, 49(1):57-61.

Binning, G., et al., Atomic force microscope *Phys. Rev. Lett.,* 1986, 56(9):930-933.

Bishop, et al., "Self-assembled monolayers: recent developments and applications" *Colloid & Interface Science,* Feb. 1996, 1:127-136.

Bottomley, L., "Scanning probe microscopy" *Anal. Chem.,* Jun. 1998, 70(12):425R-475R.

Brandow, S., et al., "Metal pattern fabrication using the local electric field of conducting atomic force microscope probe" *J. Vac. Sci. Technol.,* May/Jun. 1997, 15(3):1455-1459.

Brenner, S., et al., "Gene expression analysis by massively parallel signature sequencing (MPSS) on microbead arrays" *Nat. Biotechnol 2000,* Jun. 18(6):630-634, 2000.

Brody, E., and Gold, L., "Aptamers as therapeutic and diagnostic agents" *Molecular Biotechnology,* 2000, 74:5-13.

Bruckbauer, et al., "Writing with DNA and Protein Using a Nanopipet for Controlled Delivery" *JACS,* 2002, A-B.

Bulyk, et al., "Quantifying DNA-protein interactions by double-stranded DNA arrays" *Nature Biotechnology,* Jun. 1999, 17:573-577.

Bustamante C., et al., "Circular DNA Molecules Imaged in Air by Scanning Force Microscopy" *Biochemistry,* 1992, 31:22-26.

Bustamante, C., et al., "Biochemical and structural applications of scanning force microscopy" *Curr. Opin. Struct. Biol.,* 1994 4(5):750-760.

Carr, et al., "High-selectivity pattern transfer process for self-assembled monolayer electron beam resists" *J. Vac. Sci. Technol.,* May/Jun. 1997, 15(3):1446-1450.

Cheng, et al., "Preparation and hybridization analysis of DNA/RNA from *E. coli* on microfabricated bioelectronic chips" *Nature Biotechnology,* 1998, 16:541-546.

Chrisey et al, "Fabrication of patterned DNA surfaces" *Nucleic Acids Research,* (Oct. 1996)24(15):3040-3047.

Clark, M.W. et al., "Nanotechnology tools for functional proteomics analysis" *American Biotechnology Laboratory,* Mar. 2001, 16-18.

Colas, et al., "Genetic selection of peptide aptamers that recognize an inhibit cyclin-dependent kinase 2", *Nature,* Apr. 1996 380(11):548-550.

Colvin, et al. "Semiconductor nanocrystals covalently bound to metal surfaces with self-assembled monolayers" *J. Am. Chem. Soc.,* 1992, 114:5221-5230.

Cui, Y, et al., "Nanowire nanosensors for highly sensitive and selective detection of biological and chemical species" *Science,* 2001, 293, 1289-1292.

Dai, et al., "Nanotube Molecular Wires as Chemical Sensors" *Science,* Jan. 28, 2000, 287:622-625.

Dai, H, et al., "Controlled chemical routes to nanotube architectures" Physics and Devices, *J. Phys. Chem B,* 1999, 103:11246-11255.

Dai, H, et al., "Probing electrical transport in nanomaterials: conductivity of individual carbon nanotubes" *Science,* 1996, 272(5261):523-526.

Dammer, et al., "Binding strength between cell adhesion proteoglycans measured by atomic force microscopy" *Science,* 1995, 267:1173-1175.

Dammer, et al., "Specific antigen/antibody interactions measured by force microscopy" *Biophys. J.,* 1996, 70:2437-2441.

Delamarch, E., et al., "Patterned delivery of immunoglobulins to surfaces using microfluidic networks" *Science,* 1997, 276:779-781.

Ding. Y., Oka, T., et al., "Near-field stimulated TOF nanometric surface mass spectroscopy: characterization of Nano-localized surfaces" Joint International Meeting—200th Meeting of the Electrochemical Society, Inc., 52nd Annual Meeting of the International Society of Electrochemistry, San Francisco, California (2001).

Ding, Y., Ruggero, M. et al., "Development of UHV-STM/TOF hybrid mass analyzer system for nano-characterization of metal silicide surfaces" 198th Meeting of the Electrochemical Society, Phoenix, Arizona (2000).

DeRisi, et al., "Exploring the Metabolic and Genetic Control of Gene Expression on a Genomic Scale" *Science,* Oct. 1997, 278:680-686.

Dong, Y. and Shannon, C., "Heterogeneous Immunosensing Using Antigen and Antibody Monolayers on Gold Surfaces with Electrochemical and Scanning Probe Detection" *Anal. Chem.,* 2000, 72:2371-2376.

Dontha, N., et al., "Development of sub-micron patterned carbon electrodes for immunoassays" *J. Pharm. Biomed. Analysis,* (Feb. 1999) 19:83-91.

Dontha, N., et al., "Generation of Biotin/Avidin/Enzyme Nanostructures with Maskless Photoligography" *Anal. Chem.,* 1997, 69:619-2625.

Dubois, L. et al., "Synthesis, Structure, and Properties of Model Organic Surfaces" *Annu. Rev. Phys. Chem.,* 1992, 43:437-463.

Durbin, S., Feher, G., "Protein crystallization" *Annual Review of Phys Chemistry,* 1996, 47:171-204.

Falvo, M.R., et al., "Bending and buckling of carbon nanotubes under large strain" *Nature,* 1997, 389:582-584.

Fan, S., et al., "Self-oriented regular arrays of carbon nanotubes and their functional devices" *Science,* 1999, 283, 512.

Fang, et al., "Membrane Protein Microarrays" *JACS*, 2002, 124(11):2394-2395.

Farajian, A.A., et al., "Nonlinear Coherent Transport Through Doped Nanotube Junctions" *Physical Review*, Jun. 21, 1999, 82(25):5084-5087.

Feigon, J. "DNA triplexes, quadruplexe, and aptamers" *Clin. Chem.*, 1994, 40(4):647—647.

Florin, E., et al., "Adhesion forces between individual ligan-receptor pairs" *Science*, 1994, 264:415-417.

Fodor, S., et al., "Light-directed spatially addressable parallel chemical synthesis" *Science* 1991, 251: 767-773.

Fodor, S., et al., "Multiplexed biochemical assays with biological chips" *Nature*, 1993, 364:555-557.

Frisbie, C.D., et al., "Functional group imaging by chemical force microscopy" *Science*, 1994, 265:2071-2074.

Fritz, J., et al., "Translating biomolecular recognition into nanomechanics" *Science*, 2000, 316-318.

Fritzsche, W., et al., "Application of Atomic Force Microscopy to Visualization of DNA, Chromatin and Chromosomes" *Critical Reviews™ in Eukaryotic Gene Expression*, 1997, 7(3):231-240.

Fritzsche, W., et al., "Chicken Erythrocyte Nucleosomes Have a Defined Orientation along the Linker DNA-A Scanning Force Microscopy Study" *Scanning*, 1997, 19:42-47.

Fritzsche, W., et al., "Mapping elasticity of rehydration metaphase chromosomes by scanning force microscopy" *Ultramicroscopy*, 1997, 69:191-200.

Fritzsche, W., et al., "Ribosomes substructure investigated by scanning force microscopy and image processing" *Journal of Microscopy*, 1998, 189, Pt 1, 50-56.

Fujihira, et al., "Effect of capillary force on friction force microscopy: a scanning hydrophilicity microscope" *Chemistry Letters*, Jul. 1996, 7:499-500.

Gillen, G., Bennett, J., et al., "Molecular imaging secondary ion mass spectrometry for the characterization of patterned self-assembled monolayers on silver and gold" *Anal. Chemistry*, 1994, 66:2170-2174.

Girault, S., Chassaing, G. et al, "Coupling of MALDI-TOF mass analysis to the separation of biotinylated peptides by magnetic streptavidin beads" *Anal. Chemistry* 1996, 68:2122-2126.

Grabar, et al., "Preparation and characterization of Au colloid monolayers" *Anal. Chem.*, 1995, 67(4):735-743.

Haab, et al., "Protein microarrays for highly parallel detection and quantitation of specific proteins and antibodies in complex solutions" *Genome Biology*, 2001, 2(2)0004.1-0004.13.

Hansma, H.G., et al., "Atomic force microscopy of long and short double-stranded, single-stranded and triple-stranded nucleic acids" *Nuc. Acids Res.*, 1996, 24(4):713-720.

Hansma, H.G., et al., "Recent advances in atomic force microscopy of DNA" *Scanning* 1993, 15(5):296-9.

Hansma, H.G., Sinsheimer, R.L., et al., "Atomic force microscopy of single- and double-stranded DNA" *Nucleic Acids Research* 1992, 20:3585-90.

Hansma, P.K., et al., "Tapping mode atomic force microscopy in liquids" *Appl. Phys. Lett.*, 1994, 64(13):1738-1740.

Heller, et al., "Discovery and analysis of inflammatory disease-related genes using cDNA microarrays" *PNAS USA*, 1997, 94: 2150-2155.

Henderson, E., "Atomic force microscopy of cenventional and unconventional nucleic acid structures" *Journal of Microscopy*, 1992, 77-84.

Henderson, E., "Imaging and nanodissection of individual supercoiled plasmids by atomic force microscopy" *Nuc. Acids Res.*, 1992, 20(3):445-447.

Henderson, E., "Imaging of Living Cells by Atomic Force Microscopy" *Progress in Surface Science*, May 1994, 46(1):39-60.

Henderson, E., "Molecular force detection and spectroscopy with the atomic force microscope" *Science Progress*, 1998, 81(2):141-151.

Henderson, E., et al., "Actin Filament Dynamics in Living Glial Cells Imaged by Atomic Force Microscopy" *Science*, 1992, 257:1944-1946.

Henderson, E., et al., "New Ribosome Structure" *Science*, 1984, 255:510-512.

Henderson, E., et al., "Telomeric DNA oligonucleotides form novel intramolecular structures containing guanine-guanine base pairs" *Cell*, 1987, 51(6):899-908.

Henderson, et al., "A method for gold coating experimental detector beampipes" httb://www.Ins.cornell.edu/public/CBN/1999/CBN99-7/cbn99-7.pdf, 1999.

Hiller, et al., "Microarrayed allergen molecules: diagnostic gatekeepers for allergy treatment" *FASEB*, 2002, 16:414-416.

Hinterdorfer, P. et al., "Detection and localization of individual antibody-antigen recognition by atomic force microscopy" *PNAS*, 1996, 93:3477-3481.

Hoh, J.H., and Hansma, P.K., "Atomic force microscopy for high resolution imaging in cell biology" *Trends in Cell Biology*, 1992, 2:208-213.

Hoh, J.H., et al., "Atomic force microscopy and dissection of gap junctions" *Science*, 1991, 1405-1408.

Hoh, J.H., et al., "Quantized adhesion detected with the atomic force microscope" *J. Am. Chem. Soc.*, 1992, 114:4917-4918.

Holland, Vacuum Deposition Of Thin Films (Wiley, New York, NY, 1956) (Book Reference Net Being Provided).

Hong, et al., "A new tool for studying the in situ growth processes for self-assembled monolayers under ambient conditions" *Langmuir*, 1999, 15:7879-7900.

Hong, et al., "Multiple ink nanolithography: toward a multiple-pen nano-plotter" *Science*, 1999, 286:523-525.

Hong, S. et al. "A Nanoplotter with Both Parallel and Serial Writing Capabilities" *Science*, Jun. 9, 2000, 288:1808-1811.

Hovis, et al., "Cyloaddition chemistry and formation of ordered organic monolayers on silicone (001) surfaces" *Surface Science*, 1998, 402-404, pp. 1-7.

Hovis, et al., "Structure and bonding of ordered organic monolayers of 1,5-cyclooctadiene on the silicon (001) Surface" *J. Phys. Chem. B.*, 1997, 101:9581-9585.

Hu, et al., "Imaging the condensation and evaporation of molecularly thin films of water with nanometer resolution" *Science*, 1995, 268(5208):267-269.

Huck, et al., "Patterned polymer multilayers as etch resists" *Langmuir*, 1999, 15:6862-6867.

Ivanisevic, et al., "Dip-Pen Nanolithography on Semiconductor Surfaces" *J. Am. Chem. Soc.*, 2001, 123:7887-7889.

Iyer, et al., "The Transcription Program in the Response of Human Fibroblasts to Serum" *Science*, 1999, 283(5398):83-87.

Jackman, et al., "Fabrication of submicrometer features on curved substrates by microcontact printing" *Science*, 1995, 269: 664-666.

James, et al., "Patterned protein layers on solid substrates by thin stamp microcontact printing" *Langmuir*, 1998, 14:741-744.

Janes, et al., "Electronic conduction through 2D arrays of nanometer diameter metal clusters" *Superlattices and Microstructures,* 1995, 18(4):275-282.

Jaschke, et al., "Deposition of organic material by the tip of a scanning force microscope" *Langmuir,* 1995, 11:1061-1064.

Jin, X., Unertl, W., "Submicrometer modifications of polymer surfaces with a surface force microscope" *Applied Physics Letters,* 1992, 61(6): 657-659.

Jones, V., et al., "Microminiaturized Immunoassays Using Atomic Force Microscopy and Compositionally Patterned Antigen Arrays 66" *Anal. Chem.,* 1998, 70(7):1233-1241.

Karpovich, et al., "Direct measurement of the adsorption kinetics of alkanethioilate self-assembled monolayers on microcrystalline gold surface" *Langmuir,* 1994, 10:3315-3322.

Kim, et al., "Nanotube nanotweezers" *Science,* Dec. 10, 1999, 286:2148-2150.

Knezevic et al., "Proteomic profiling of the cancer microenvironment by antibody arrays" *Proteomics,* 2001,. 1:1271-1278.

Kochanek, et al., "Transcriptional silencing of human ALU sequences and inhibition of protein binding in the box B regulatory elements by 5'CG3" methylation" *FEBS Lett.,* 1995, 360(2):115-120 [PMID 7875314] Abstract.

Komeda, et al., "Octadecyltrichlorosilane self-assembled-monolayer islands as a self-patterned-mask for HF etching of $SiO_2$ on Si" *J. Vac. Sci. Technol A.,* 1998, 16(3):1680-1685.

Kumar, et al., "The use of self-assembled monolayers and a selective etch to generate patterned gold features" *J. Am. Chem. Soc.,* 1992, 114:9188-9189.

Lahiri, et al., "Patterning ligands on reactive SAMs by microcontact printing" *Langmuir,* 1999, 15:2055-2060.

Laibinis et al., "ω-terminated alkanethiolate monolayers on surfaces of copper, silver, and gold have similar wettabilities[1]" *J. Am. Chem. Soc.,* 1992, 114: 1990-1995.

Lal, R. and John, S.A., "Biological applications of atomic force microscopy" *Am J. Physiology,* 1994, 266(1):1-21.

Lanio, T., et al., "PCR-based random mutagenesis method using spiked oligonucleotides to randomize selected parts of gene without any wild-type background" *Biotechniques,* 1998, 25(6):958-965.

Lee, et al., "Nanometer-scale lithography on H-passivated Si(100) by atomic force microscope in air" *J. Vac. Sci. Technol. A.,* 1997, 15(3):1451-1454.

Lee, G. et al. "Direct measurement of the forces between complementary strands of DNA" *Science,* 1994, 266:771-773.

Lercel, et al. "Self-assembled monolayer electron-beam resists on GaAs and $SiO_2$" *J. Vac. Sci. Technol. B.,* 1993, 11(6): 2823-2828.

Lercel, et al., "Sub-10nm lithography with self-assembled monolayers" *Appl. Phys. Lett.,* 1996, 68(11):1504-1506.

Liu, et al., "Nanofabrication of self-assembled monolayers using scanning probe lithography" *Acc. Chem. Res.,* 2000, 33(7):457-466.

Lo, et al., "Organic and inorganic contamination on commercial AFM cantilevers" *Langmuir,* 1999, 15:6522-6526.

Lüthi, et al., Parallel nanodevice fabrication using a combination of shadow mask and scanning probe methods: *Applied Physics Letters,* 1999, 75(9):1314-1316.

Lutwyche, et al., "5X5 2D AFM cantilever arrays a first step toward Terabit storage device" *Sensors and Actuators,* 1999, 73:89-94.

Lynch, M., et al., "A Reliable Preparatioon Method for Imaging DNA by AFM" *Microscopy Today,* 1999, 99(9) 1 pg.

Lyubchenko, Y.L., et al., "Atomic force microscopy of DNA and bacteriophage in air, water and propanol: The role of adhesion forces"*Nuc. Acids. Res.,* 1993, 21(5):1117-1123.

Macaya, et al., "Thrombin-binding DNA aptamer forms a unimolecular quadruplex structure in solution" *PNAS USA,* Apr. 1993, 90:3745-3749.

MacBeath, G. and Schreiber, S.L., "Printing Proteins as Microarrays for High-Throughput Function Determination" *Science,* Sep. 8, 2000, 289:1760-1763.

Magno, R., Bennett, B., "Nanostructure patterns written in III-V semiconductors by an atomic force microscope" *Applied Physics Letters,* 1997, 70(14):1855-1857.

Malmborg, et al., "Real Time Analysis of Antibody-Antigen Reaction Kinetics", *Scand. J. Immunol.,* 1992, 35:634-650.

Marsh, T.C., et al., "A new DNA nanostructure imaged by scanning probe microscopy" *Nuc. Acids Res.* 1995, 23(4):696-700.

Marsh, T.C., et al., "G-wires: Self-assembly of a telometic oligonucleotide, d(GGGGTTGGGG), into large superstructures" *Biochemistry* 1994, 33:10718-10724.

Martin, B., et al., "Ortogonal Self-Assembly on Colloidal Gold-Platinum Nanorods" *Advanced Materials,* 1999, 11:1021.

Matteucci, et al., "Synthesis of deoxyoligonucleotides on a polymer support 1" *J. Am. Chem. Soc.,* 1981, 103:3185-3191.

Maynor, et al., "Au :Ink" for AFM "Dip-Pen" Nanolithography *Langmuir,* 2001, 17:2575-2579.

Mazzola, L., "Discrimination of DNA hybridization using chemical force microscopy" *Biophysical Journal,* 1999, 76:2922-2933.

Mazzola, L., "Imaging biomolecule arrays by atomic force microscopy" *Biophysical Journal,* 1995, 68:1653-1660.

McEuen, et al., "Crossed Nanotube Junctions" *Science,* Apr. 21, 2000, 288:494-497.

Meister, et al., "Nanoscale Dispensing of Liquids through Cantilevered Probes" *MNE '02,* Lugano, Switzerland, Sep. 16-19, 2002.

Mendoza, et al., "High-Throughput Microarray-Based Anzyme-Linked Immunosorbent Assay (ELISA)" *BioTechniques,* 1994, 27(4):778-788.

Meyer, G. and N.M. Amer, "Novel optical approach to atomic force microscopy" *Appl. Phys. Lett.,* 1988, 53:1045-1047.

Minne, et al., "Centimeter scale atomic force microscope imaging and lithography" *Applied Physics Letters,* 1998, 73(12):1742-1744.

Minne, S.C., et al., "Automated parallel high-speed atomic force microscopy" *Appl. Phys. Lett.,* 1998, 72(18):2340-2342.

Mirkin, et al., "Dip-Pen Nanolithography: Controlling Surface Architecture on the Sub-100 Nanometer Length Scale" *Chemphyschem,* 2001, 2:37-39.

Mirkin, et al., "Programming the Assembly of Two- and Three-Dimensional Architectures with DNA and Nanoscale Inorganic Building Blocks" Invited Contribution from Recipient of ACS Award in Pure Chemistry *Inorg. Chem.,* 2000, 39:2258-2272.

Mosher, C., et al., "NanoArrays, The Next Generation Molecular Array Format for High Throughput Proteomics, Diagnostics and Drug Recovery" *JALA,* 2000, 5(5):75-83.

Moy, et al., "Intermolecular Forces and Energies Between Ligands and Receptors" *Science,* 1994, 266:257-259.

Moy, V.T., et al., "Probing the forces between complimentary strands of DNA with the atomic force microscope" *SPIE,* 1995, 2384:2-12.

Mueller, et al., "Atomic force microscopy deposition of poly-1-lysine structures onto lipid bilayers supported by mica" *Langmuir,* 2000, 16:9568-9570.

Müller, et al., "Nanostructuring of alkanethiols with ultrastrap field emitters" *J. Vac. Sci. Technol. B.,* 1995, 13(6):2846-2849.

Murray, et al., "Atomic force microscopy of biochemically tagged DNA" *Proc. Natl., Acad. Sci.,* 1993, 90:3811-3814.

Musil, C., Nanostructuring of gold electrodes for immunosensing applications: *J. Vac. Sci. Technol. B.,* 1995, 13(6):2781-2786.

Niu, et al., "Atomic force microscopy of DNA-colloidal gold and DNA-protein complexes" *SPIE Advances in DNA Sequencing Technology,* 1993, 1891:71-77.

Noy, et al., "Chemical force microscopy: exploiting chemically-modified tips to quantify adhesion, friction, and functional group distributions in molecular assemblies" *J. Am. Chem.,* 1995, 117:7943-7951.

Noy, et al., "Chemically-sensitive imaging in tapping mode by chemical force microscopy: relationship between phase lag adhesion" *Langmuir,* 1998, 14:1508-1511.

Nuzzo, R., "Spontaneously organized molecular assemblies. 3. Preparation and properties of solution adsorbed monolayers of organic disulfides on gold surfaces" *J. Am. Chem. Soc.,* 1987, 109:2358-2368.

Nyffenegger, et al., "Nonometer scale surface modification using the scanning probe microscope: progress since 1991" *Chem. Rev.,* 1997, 97:1195-1230.

O'Brien, J., et al., "Immunosensing Platoforms Using Spontaneously Absorbed Antibody Fragments on Gold" *Analytical Chemistry,* 2000, 72(4)703-710 [PMID 10701253] Abstract.

Oshio, T. et al., "Atomic force microscopy detection system using an optical fiber heterodyne interferometer free from external disturbances" *Ultramicroscopy* 42-44 (Jul. 1992) 310-314.

Paweletz, et al., "Reverse phase protein microarrays which capture disease progression shoe activation of pro-survival pathways at the cancer invasion front" *Oncogen,* 2001, 20:1981-1989.

Pawlak, et al., "Zeptosens' protein microarrays: A novel high performance microarray platform for low abundance protein analysis" *Proteomics,* 2002,. 2:383-393.

Perkins, et al., "Fabrication of 15 nm wide trenches i Si by vacuum scanning tunneling microscope lithography of an organosilane self-assembled film and reactive ion etching" *Appl. Phys. Lett.,* 1996, 68(4):550-552.

Pfannschmidt, et al., "Sequence-specific labeling of superhelical DNA by triple helix formation and psoralen crosslinking" *Nucleic Acids Research,* 1996 24(9):1702-1709.

Piner, et al., "Improved imaging of soft materials with modified AFM tips" *Langmuir,* 1999, 15:5457-5460.

Piner, R.D., et al., "Dip-Pen Nanolithography" *Science,* Jan. 29, 1999,283(5402):661-663.

Piner, Richard, "Effect of water on lateral force microscopy in air" *Langmiur,* 1997, 13:6864-6868.

Putnam, C.A.J., "Tapping atomic force microscopy in liquids" *Appl. Phys. Lett.,* 1994, 64(18):2454-2456.

Qin, et al., Fabrication of ordered two-dimensional arrays of micro- and nanoparticles using patterned self-assembled monolayers as templates: *Adv. Matter,* 1999, 11(17):1433-1437.

Rankin, P.C. Wilson, A.T. "The Surface Chemistry of the Mica-Aluminum-Sulfate System" *Journal of Colloid and Interface Science,* (1969) 30(3):277-282.

Reed, et al., "Conductance of molecular junction" *Science,* 1997, 278:252-254.

Rief, et al., "Reversible unfolding of individual Titan Ig-domains by AFM" *Science,* 1997, 276:1109-1111.

Rief, M., et al., "Single Molecule Force Spectroscopy on Polysaccharides by Atomic Force Microscopy" *Science,* 1997, 275:1295-1297.

Rief, M., et al., "The mechanical stability of immunoglobulin and fibronectin III domains in the muscle protein titin measured by atomic force microscopy" *Biophysical Journal,* 1998, 3008-3014.

Robinson, et al., Autoantigen microarrays for multiplex characterization of autoantibody responses *Nature Medicine,* Mar. 2002, 8(3):1-7.

Santos, et al., "Probing hydrophobic interactions of surfaces and macromolecules with atomic force microscope" *Book of Abstracts,* 214 ACS National meeting, Sep. 7-11, 1997, PHYS-248.

Sastry, et al., "Formation of patterned hetrocolloidal nanoparticle thin films" *Langmuir,* 2000, 16:3553-3556.

Schaus, S., et al., "Cell Viability and Probe-Cell Membrane Interactions of XR1 Glial Cells Imaged by Atomic Force Microscopy" *Biophysical Journal,* Sep. 1997, 73:1205-1214.

Schena, et al., "Parallel human genome analysis : Microarray-based expression monitoring of 1000 genes" *PNAS USA,* 1996, 93:10614-10619.

Schena, M., *Microarray Biochip Technology,* Eaton Publishing, NatickMA 2000. (Book Reference Not Being Provided).

Schoer, et al., "Scanning probe lithography. 4. Characterization of scanning tunneling microscope-induced patterns in n-Alknethiol self-assembled monolayers" *Langmuir,* 1997, 13:2323-2332.

Schumacher, et al., "Nanomachining of mesoscopic electronic devices using an atomic force microscope" *Applied Physics,* 1999, 75(8):1107-1109.

Schwartz, et al. "Meniscus Force Nanografting: Nanoscopic Patterning of DNA" *Langmuir,* 2001, 17:5971-5977.

Schwartz, et al., "Molecular Transport from an Atomic Force Microscope Tip: A Comparative Study of Dip-Pen Nanolithography" *Langmuir,* American Chemical Society, Nov. 6, 2001.

Schweitzer, et al., "Multiplexed protein profiling on microarrays by rolling-circle amplification" *Nature Biotechnology,* Apr. 2002, 20:359-365.

Shaiu, W.L., et al., "Atomic Force Microscopy of Oriented Linear DNA Molecules Labeled with 5nm Gold Spheres" *Nuc. Acids Res.,* 1993, 21(1):99-103.

Shaiu, W.L., et al., "Visualization of circular DNA molecules labeled with colloidal gold spheres using atomic force microscopy" *J. Vac. Sci. Technol. A.,* 11(4):820-823.

Sheehan, et al., "Thiol diffusion and the role of humidity in "dip pen" nanolithography" *Physical Review Letters,* Apr. 15, 2002, 88(15):156104-1-156104-4.

Sheen, et al., "A new class of organized self-assembled monolayers: alkane thiols on GaAs (100)" *J. Am. Chem. Soc.,* 1992, 114:1514-1515.

Sherman, Chemical Vapor Deposition For Microelectornices: Principles, Technology and Applications (Noyes, Park Ridges, NJ, 1987). (Book Reference Not Being Provided).

Shlyakhtenko, L.S.,. et al., "Structure and dynamics of supercoil-stabilized DNA cruciforms" *J. Mol. Biol.*, 1998, 280(1):61-72.

Shlyakhtenko, L.S., Gall, A.A., et al., "Atomic force microscopy imaging of DNA covalently immobilized on a functionalized mica substrate" *Biophysical Journal*, Jul. 1999, 77:568-576.

Silzel, et al., "Mass-sensing, multianalyte microarray immunoassay with imaging detection" *Clinical Chemistry*, 1998, 44(9):2036-2043.

Smalley, et al., "Nanotube Device" *Science*, Oct. 3, 1997, 278:100-103.

Smith et al., "Overstretching B-DNA: the elastic response of individual double-stranded and single stranded DNA molecules" *Science*, Feb. 9, 1996, 271:795-799.

Snow, et al., "High speed patterning of a metal silicide using scanned probe lithography" *Applied Physics Letters*, 1999, 75(10):1476-1478.

Soh, H., et al., "Integrated nanotube circuits: controlled growth and ohmic contacts to single-walled-carbon nanotubes" *Appl. Phys. Letts.,* 1999, 75(5): 627-629.

Sondag-Huethorst, et al., "Generation of electrochemically deposited metal patterns by means of electron beam (nano)lithography of self-assembled monolayer resists" *Appl. Phys. Lett.* 1994, 64(3):285-287.

Southern, E.M., "Detection of specific sequences among DNA fragments separated by gel electrophoresis" *J. Mol. Biol.* 1975, 98:503-517.

Spectroscopy Europe—News Feb./Mar. 2002, 6 pages, http://www.spectroscopyeurope.com/news14_1.html.

Spence, J., Weierstall, U., et al., "Atomic species identification in scanning tunneling microscopy by time of flight spectroscopy" *J. Vac. Sci. Tech.*, 1996, B 14(3):1587-1590.

Sreekumar, et al., "Profiling of cancer cells using protein microarrays: Discovery of novel radiation-regulated proteins" *Cancer Research*, 2001, 61:7585-7593.

Steiner, et al., "Adsorption of alkanenitriles and alkanedinitriles on gold and copper" *Langmuir*, 1992, 8:2271-2777.

Stöckle, R., Setz, P. "Nanoscale Atmospheric Pressure Laser Ablation-Mass Spectrometry" *Anal. Chem.,* 2001, 73(7):1399-1402.

Su, et al., "Moving beyond Molecules: Patterning Solid-State Features via Dip-Pen Nanolithography with Sol-Based Inks" *JACS,* 2002, 124(8):1560-1561.

Sun, et al., "Nanoscale Molecular Patterns Fabricated by Using Scanning Near-Field Optical Lithography" *JACS,* 2002, 124(11):2414-2415.

Tang, K., Fu, D., et al., "Matrix-assisted laser desorption/ionization mass spectrometry of immobilized duplex DNA probes" *Nucleic Acids Research,* 1995, 23(16):3126-3131.

Tans, et al., "Room-temperature transistor based on a single carbon nanotube" *Nature*, May 7, 1998, 393:49-52.

Tarlov, M.J., Newman, J.G., et al., "Static secondary ion mass spectrometry of self-assembled alkanethiol monolayers on gold" *Langmuir*, 1992, 8:1398-1405.

Tien, et al., "Microfabrication through electrostatic self-assembly" *Langmuir*, 1997, 13:5349-5355.

Troughton, E., Bain, C., et al., "Monolayer films prepared by the spontaneous self-assembly of symmetrical and unsymmetrical dialkyl sulfides from solution onto gold substrates: Structure, properties and reactivity of constituent functional groups" *Langmuir,* 1988, 4:365-385.

Tsukamoto, et al. "Twin-probe scanning tunneling microscope" *Rev. Sci. Instrum.*, Jul. 1991, 62(7):767-1771.

Uetz, P., et al., "A comprehensive analysis of protein—protein interactions in *Saccharomyces cerevisiae*" *Nature*, Feb. 10, 2000, 403(6770):623-627.

Ulman, Abraham, "Formation and structure of self-assembled monolayers" *Chem. Rev.,* 1996, 96:1533-1554.

ULMAN, An Introduction To Ultrathin Organic Films: From Langmuir-Blodgett to Self-Assembly (Academic, Boston 1991) (Alkanethiols on gold). (Book Reference Not Being Provided).

Vesenka, J. et al., "A substrate preparation for reliable imaging of DNA molecules with the scanning force microscope" *Ultramicroscopy,* 1992, 42-44:1243-1249.

Vesenka, J., et al., "Colloidal gold particles as an incompressable atomic force microscope imaging standard for assessing the compressability of biomolecules" *Biophys. J.,* 1993, 65:992-997.

Vesenka, J., et al., "Combining optical and atomic force microscopy for life sciences research" *BioTechniques,* 1995, 19(2):240-253.

Vettiger, et al., "Ultrahigh density, high-data-rate NEMS-based AFM data storage system" *Microelectronic Engineering,* 1999, 46:11-17.

Vezenov, Dmitri, "Force titrations and ionization state sensitive imaging of functional groups in aqueous solutions by chemical force microscopy" *J. Am. Chem. Soc.,* 1997, 119:2006-2015.

Vossmeyer, et al., "Combinatorial approaches toward patterning nanocrystals" *Journal of Applied Pysics,* 1998, 84(7):3664.

Wadu-Mesthrige, et al., "Fabrication and imaging of nanomneter-sized protein patterns" *Langmuir,* 1999, 15:8580-8583.

Wallraff, et al., "Lithographic imaging techniques for the formation of nanoscopic features" *Chem. Rev.,* 1999, 99:1801-1821.

Walters, D.A., Hampton, A.D., et al. "Atomic force microscope integrated with a scanning electron microscope for tip fabrication" *Applied Physics Letters,* Aug. 8, 1994, 65(6):787-789.

Wang, et al., "Nanometer scale patterning and pattern transfer on amorphous Si, crystalline Si, and $SiO_2$ surfaces using self-assembled monolayers" *Appl. Phys. Lett.,* 1997, 70(12):1593-1595.

Weierstall, U. Spense, J. "Atom species identification in STM using an Imaging Atom-Probe technique" *Surface Science* 1998, 398: 267-279.

Whitesides, et al., "Self-assembled monolayers and lithography" *Nanophase Chemistry* 1995, 39: 109-122.

Wilbur, et al., "Scanning force microscopes can image patterned self-assembled monolayers" *Langmuir,* 1995, 11:825-831.

Williamson, et al., "G-quartets in biology: Reprise" *PNAS USA*, Apr. 15, 1993, 90(8):3124—3124.

Williamson, et al., "Monovalent cation-induced structure of telomeric DNA: The G-quartet model" *Cell,* 1989, 59(5):871-880.

Wilson, et al., "Surface organization and nanopatterning of collagen by dip-pen nanolithography" *PNAS*, Nov. 20, 2001, 98(24):13660-13664.

Wong, S., et al., "Covalently functionalized nanotubes as nanometre-sized probes in chemistry and biolog" *Nature*, 1998, 394:52-55.

Wong, S., et al., "Covalently functionalized single-walled carbon nanotube probe tips for chemical force microscopy" *Journal of the American Chemical Society*, 1998, 120:8557-8558.

Wong, S., et al., "Functionalization of carbon nanotube AFM probes using tip-activated gases" *Chem Physics Letters*, 1999, 306:219-225.

Xia, et al., "A selective etching solution for use with patterned self-assembled monolayers of alkanethiolates on gold" *Chem. Mater.*, 1995, 7:2332-2337.

Xia, et al., "Complex optical surfaces formed by replica molding against elastomeric masters" *Science*, 1996, 273: 347-349.

Xia, et al., "Pattern transfer: self-assembled monolayers as ultrathin resists" *Microelectronic Engineering*, 1996, 32:255-268.

Xia, et al., "Soft lithography" *Agnew Chem. Int. Ed.*, 1998, 37:551-575.

Xia, et al., "Unconventional methods for fabricating and patterning nanostructures" *Chem. Rev.*, 1999, 99:1823-1848.

Xu, et al., "Fabrication of nanometer scale patterns within self-assembled monolayers by nanografting" *Langmuir*, 1999, 15:7244-7251.

Xu, et al., Nanometer-scale fabrication by simultaneous nanoshaving and molecular self-assembly: *Langmuir*, 1997, 13:127-129.

Xu, et al., "Wetting and capillary phenomena of water on mica" *J. Phys. Chem. B.*, 1998, 102:540-548.

Yan Li, et al., "Electrochemical AFM "Dip-Pen" Nanolithography" *J. Am. Chem., Soc.* 2001, 123:2105-2106.

Yan, et al. "Patterning a performed, reactive SAM using microcontact printing" *J. Am. Chem. Soc.*, 1998, 120:6179-6180.

Yan, et al., "Patterning thin films of poly(ethylene imine) on a reactive SAM using microcontact printing" *Langmuir*, 1999, 15:1208-1214.

Ying, et al., "Programmable Delivery of DNA through a Nanopipet" *Anal. Chem.*, 2002, 74:1380-1385.

Youil, R., Screening for mutations by enzyme mismatch cleavage with T4 endonuclease VII *PNAS USA*, 1995, 92(1):87-91.

Zhong, Q., et al., "Fractured polymer/silica fiber surface studied by tapping mode atomic force microscopy" *Surf. Sci. Lett.*, Jan. 3, 1993, 290: L 688-L692.

Zhu, et al., "Analysis of yeast protein kinases using protein chips" *Nature Genetics*, 2000, 26:283-289.

Zhu, et al., "Global Analysis of Protein Activities Using Proteome Chips" *Science*, Sep. 2001, 293(14):2101-2105.

* cited by examiner

ELECTRONIC ENDOSCOPE FOR HIGHLIGHTING BLOOD VESSEL

BACKGROUND OF THE INVENTION

This application claims the priority of Japanese Patent Applications No. 2002-21076 filed on Jan. 30, 2002 and No.2001-295271 filed on Sep. 27, 2001 which are incorporated herein by reference.

1. Field of the Invention

The present invention relates to an electronic endoscope, and more particularly, to image processing of an electronic endoscope capable of displaying blood vessels inside the body of an examinee in an easily viewable condition.

2. Description of the Related Art

An electronic endoscope irradiates an object under observation with illuminating light to capture an image thereof through an objective optical system, takes in the image using an image pickup element such as a CCD (Charge Coupled Device) and displays this object image on a monitor, etc. In recent years, this type of electronic endoscope incorporates a power scaling mechanism in the above-described objective optical system and displays the optically magnified object image. At the same time, the image is electronically magnified by the electronic zoom function, which allows details of a focused area to be clearly observed with the magnified image shown on the monitor, etc.

SUMMARY OF THE INVENTION

Figure 8:
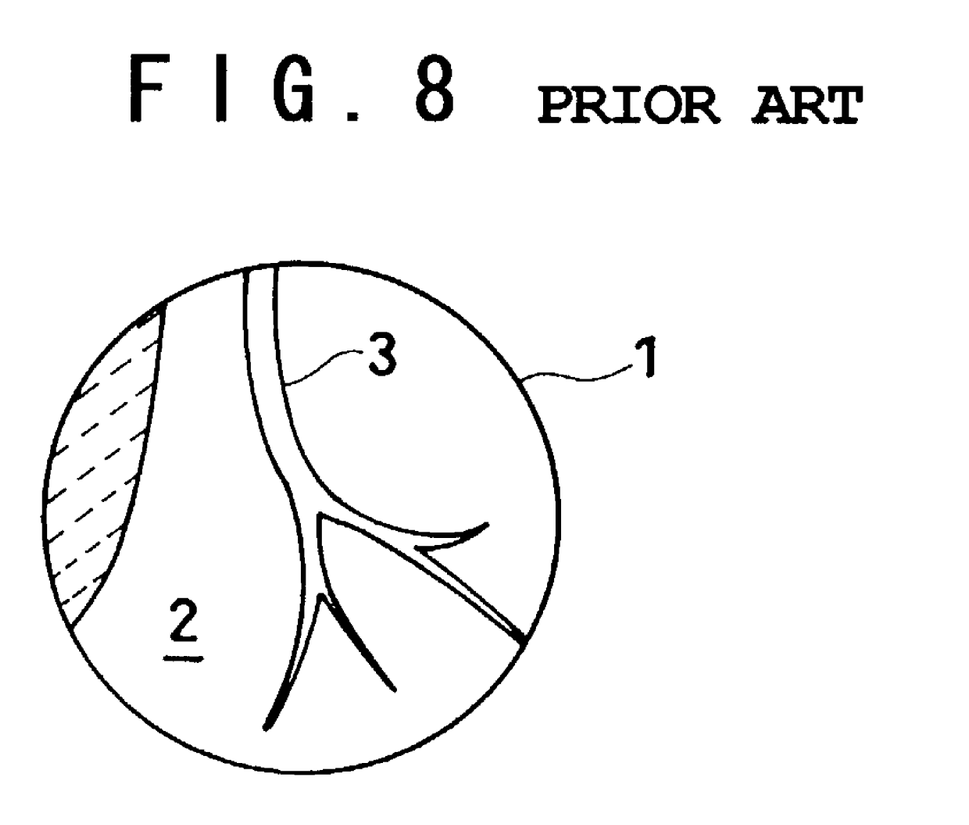
FIG. 8 illustrates a magnified image of an object displayed by a conventional electronic endoscope.

By the way, image pickup targets of the electronic endoscope are often objects inside a living body such as digestive organs, and as shown in FIG. 8, a magnified object image 1 (displayed on a monitor, etc.) includes a blood vessel (especially capillary blood vessel) 3 in a mucous membrane 2 and a blood circulation state and a concentration situation of this blood vessel (blood) 3 constitute important observation targets in making a diagnosis of a focus or identifying cancerous tissue, etc. On the other hand, since the interior of the living body has pink or reddish coloring, making a distinction between the blood vessel 3 and other tissue such as the mucous membrane 2 tends to become difficult. Thus, if the blood vessel 3 could be displayed clearly, it will be possible to provide information useful for observation and diagnosis of the living body.

The present invention has been achieved in view of the above-described problems and it is an object of the present invention to provide an electronic endoscope capable of clearly displaying an image of a specific object such as a blood vessel in sharp contrast to other tissue such as mucous membranes.

To attain the above object, an electronic endoscope according to the present invention includes a color signal processing circuit that forms a predetermined signal for color display based on a signal obtained by an image pickup element, a blood vessel edge detection circuit that inputs the predetermined signal output from said color signal processing circuit and detects both ends of a blood vessel in the width direction, a multiplier that multiplies each of both ends of the blood vessel obtained by said blood vessel edge detection circuit by a predetermined coefficient, and is characterized in that a blood highlighting circuit is formed of the above-described blood edge detection circuit and the above-described multiplier.

Here, the above-described blood vessel highlighting circuit can be constructed in such a way that the above-described blood vessel edge detection circuit detects the down edge section and up edge section at both ends of the blood vessel in the width direction, multiplies said down edge section by a coefficient which is smaller than 1 and multiplies the up edge section by a coefficient which is larger than 1.

Furthermore, the above-described color signal processing circuit can form red, green and blue color signals, while the above-described blood vessel highlighting circuit can detect both ends of the blood vessel using the above green signal and multiply at least the red signal by the coefficient for these both ends of the blood vessel.

According to the above-described aspect of the present invention, the color signal processing circuit forms R (red), G (green) and B (blue) color signals, etc. and detect the down edge section and up edge section of both ends of the blood vessel in the width direction using, for example, the image of the G signal of the color signals. A coefficient smaller than 1 is given to this down edge section, a coefficient larger than 1 is given to the up edge section and a coefficient of 1 is given to the rest and for example, the R and B image signals are multiplied by these coefficients. This results in the down edge section signal lowered from its normal level and the up edge section signal lifted from its normal level, which produces high contrast at both ends of the blood vessel and allows the blood vessel even in a mucous membrane to be displayed clearly. While both ends of the blood vessel can also be detected by the above blood vessel edge detection circuit using the red signal, using the green signal has an advantage of making clearer the difference between the blood vessel and mucous membrane.

Furthermore, there is also a case where the above-described color signal processing circuit forms a brightness signal and color difference signal and in such a case, it is also possible to allow the above-described blood vessel highlighting circuit to detect both ends of the blood vessel using the brightness signal and multiply the color difference signal or red or blue color signal by the coefficient corresponding to both ends of this blood vessel.

Another aspect of the present invention is characterized by including a color difference signal formation circuit that forms two color difference signals based on the signal obtained by the image pickup element, a specific object extraction circuit that inputs the color difference signals output from said color difference signal formation circuit and extracts a phase signal of a specific object color on a coordinate system in which one of these color difference signals is set on the vertical axis and the other is set on the horizontal axis, and a level correction circuit that increases/decreases the level of the signal obtained from said specific object extraction circuit and adjusts chroma of the specific object color. In this aspect, it is possible to assume an R (red)-Y (brightness) signal and B (blue)-Y signal as the color difference signals and a blood vessel as the specific object.

According to the above-described aspect, in the case where the phase of a blood vessel color is $\theta_1$ on a coordinate system in which R-Y is set on the vertical axis and B-Y is set on the horizontal axis, the aspect assumes $\theta_1$ to be a reference value and extracts a signal whose phase value of (R-Y)/(B-Y) matches the reference value $\theta_1$. On the other hand, the color signal of a membrane becomes a signal with a phase different from the phase of the blood vessel color (e.g., $\theta_2$). Then, the signal level of this blood vessel is amplified, whereby the chroma of the blood vessel color is increased and as a result, the blood vessel is displayed in high contrast even in the mucous membrane.

BRIEF DESCRIPTION OF THE DRAWINGS

FIG. 3A to FIG. 3C illustrate blood vessel highlighting processing states of the first embodiment, FIG. 3A illustrate a G image, FIG. 3B illustrates an R image and FIG. 3C illustrates a final image;

DETAILED DESCRIPTION OF THE PREFERRED EMBODIMENTS

First Embodiment

Figure 1:
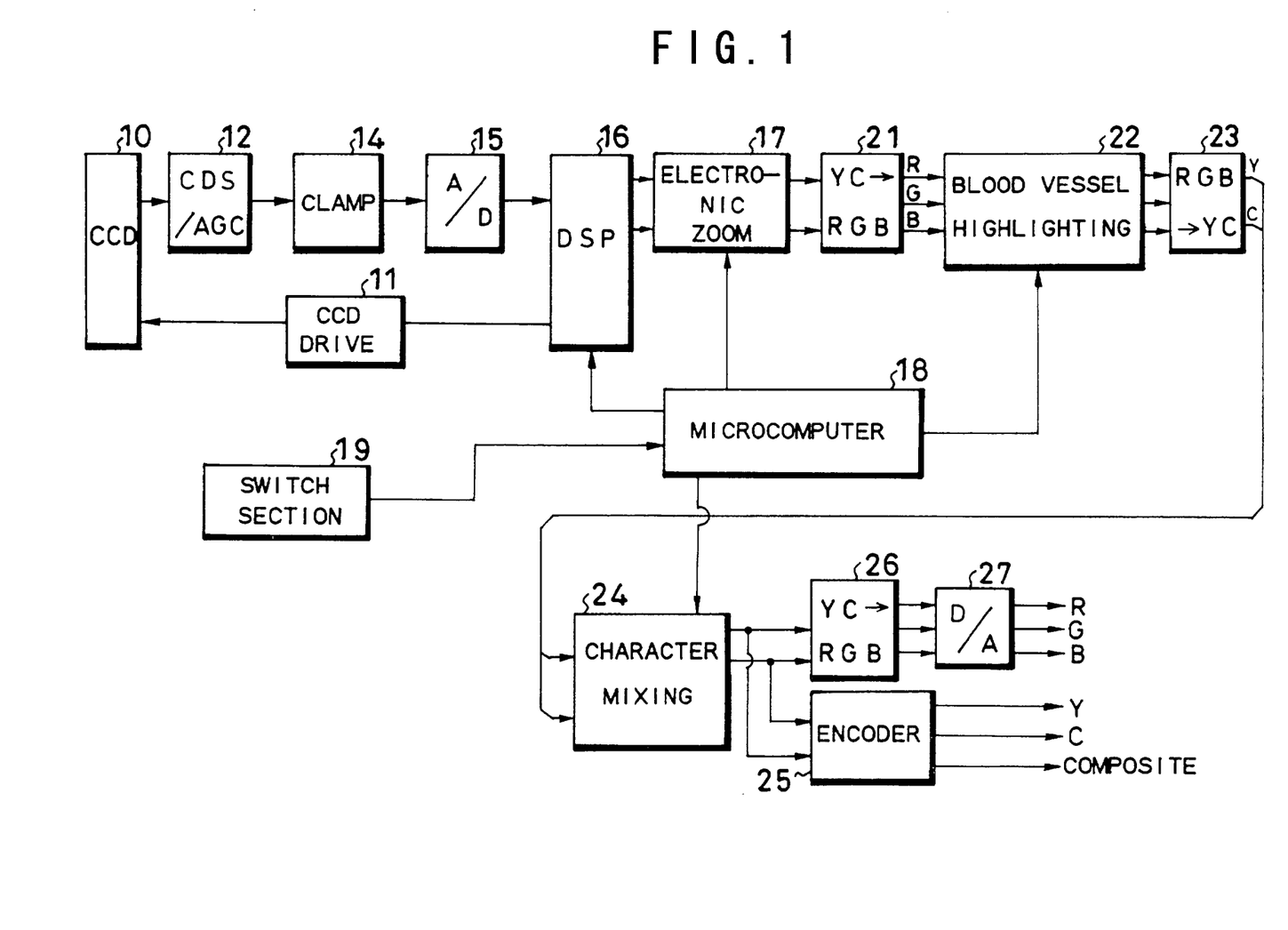
FIG. 1 is a block diagram showing internal configurations of a scope and processor unit in an electronic endoscope according to a first embodiment of the present invention.
Figure 2:
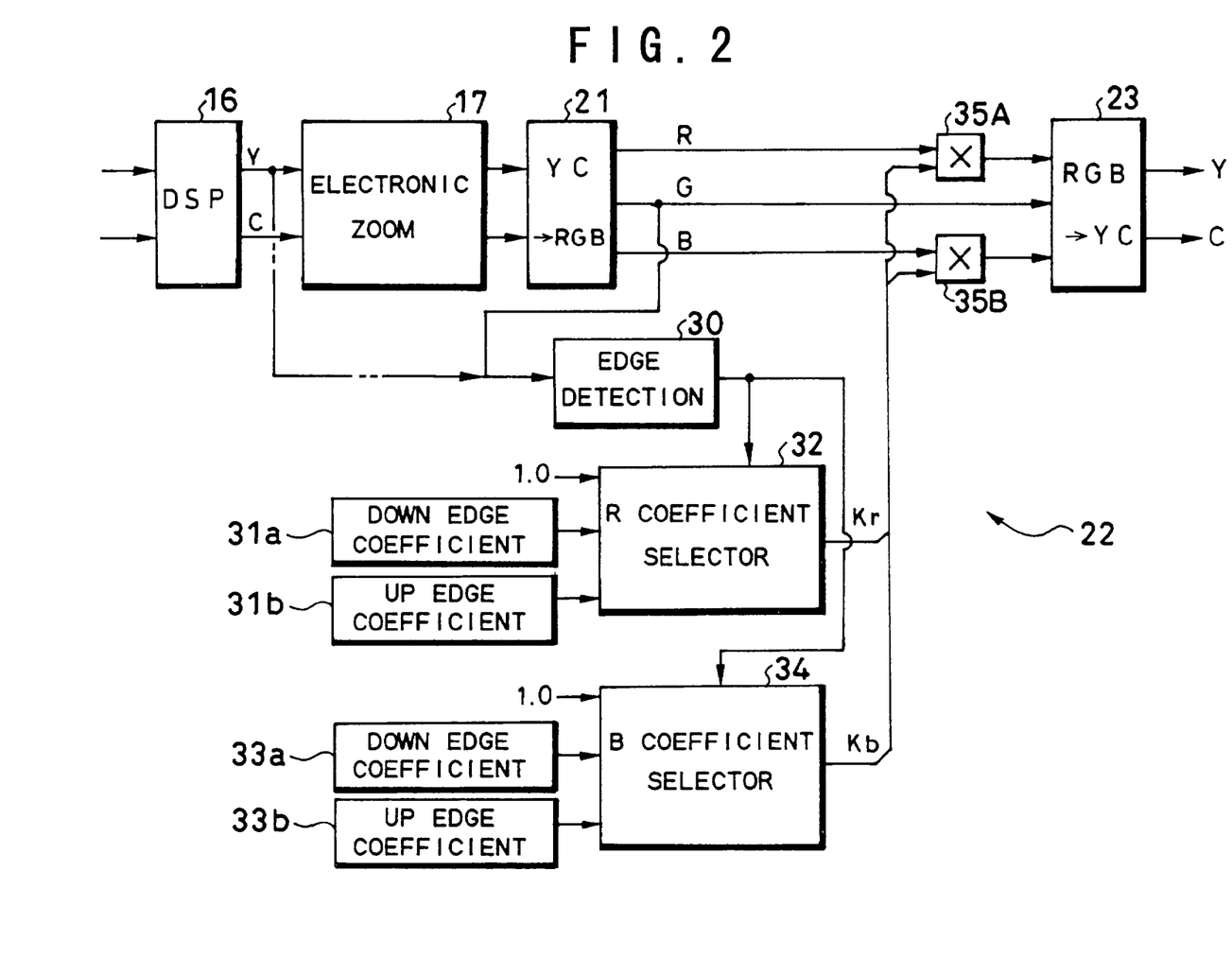
FIG. 2 is a block diagram showing a configuration related to blood vessel highlighting of the electronic endoscope according to the first embodiment.

FIG. 1 shows configurations of a scope and processor unit (color signal processing circuit) in an electronic endoscope according to a first embodiment, FIG. 2 shows a configuration related to blood vessel highlighting of this electronic endoscope and though not shown in these drawings, this electronic endoscope is also provided with a light source unit, a monitor and a recorder, etc. and adopts, for example, a synchronous system as an image pickup system. In FIG. 1, a CCD 10 which is an image pickup element, is provided at a tip of the scope and this CCD 10 captures an image of an object through color filters on a pixel-by-pixel basis (e.g., Mg (magenta), G (green), Cy (cyan) and Ye (yellow)). That is, when light from the above-described light source unit is irradiated from the tip of the scope onto the object through a light guide, the image of this object is taken by the CCD 10. Furthermore, if an objective optical system with a built-in power scaling movable lens is provided in front of this CCD 10, it is possible to obtain a magnified image of the object by driving this power scaling lens.

The above-described CCD 10 is connected to a CCD drive circuit 11 for reading charges stored as image pickup signals and this CCD 10 is followed by a CDS (Correlated Double Sampling)/AGC (Automatic Gain Control) 12 and this CDS/AGC 12 applies correlated double sampling to an output signal of the CCD 10 and applies predetermined amplification processing as well. This CDS/AGC 12 is provided with a DSP (Digital Signal Processor) 16 and an electronic zoom circuit 17 via a clamp circuit 14 and an A/D (analog/digital) converter 15, and a microcontroller 18 is provided to control these circuits in a concentrated manner.

This DSP 16 performs various types of processing such as white balance, gamma correction and forms a Y (brightness) signal and color difference (C) signals of R (red)-Y and B (blue)-Y. The electronic zoom circuit 17 magnifies the image obtained by the DSP 16 based on, for example, a zoom switch placed at a switch section 19.

This electronic zoom circuit 17 is followed by an RGB color conversion circuit 21 that converts the above-described Y signal and C signals to R (red), G (green) and B (blue) signals. That is, the DSP 16 in this embodiment forms a Y signal, C signals of R-Y and B-Y by performing color conversion operations from signals obtained via various color filters of Mg, G, Cy and Ye. By performing further color conversion operations on these Y and C signals, R, G and B color signals are obtained.

Then, this first embodiment is provided with a blood vessel highlighting circuit 22 to clearly display blood vessels in the form of inputting signals of this RGB color conversion circuit 21, which will be described in more detail later using FIG. 2. This blood vessel highlighting circuit 22 is followed by a YC color conversion circuit 23 that inversely converts the R, G and B signals to a Y signal and C signals, and further connected to a character mixing circuit 24 that mixes characters such as patient information with an image signal, an encoder 25 that processes outputs to the monitor based on the Y signal and C signals, an RGB color conversion circuit 26 that converts the Y signal and C signals to R, G and B signals and a D/A converter 27, etc.

As shown in FIG. 2, the blood vessel highlighting circuit 22 is provided with an edge detection circuit 30 that detects a down edge section and an up edge section of blood vessels from the image of the G signal entered, coefficient generation circuits (or can also be memory, etc.) 31a and 31b that give a down edge coefficient and up edge coefficient Kr to the R signal, an R coefficient selector 32 that selects these coefficients (and 1) Kr, coefficient generation circuits 33a and 33b that give a down edge coefficient and up edge coefficient Kb to the B signal, a B coefficient selector 34 that selects these coefficients (and 1) Kb, multipliers 35A and 35B that multiply coefficients Kr and Kb.

Figure 3A:
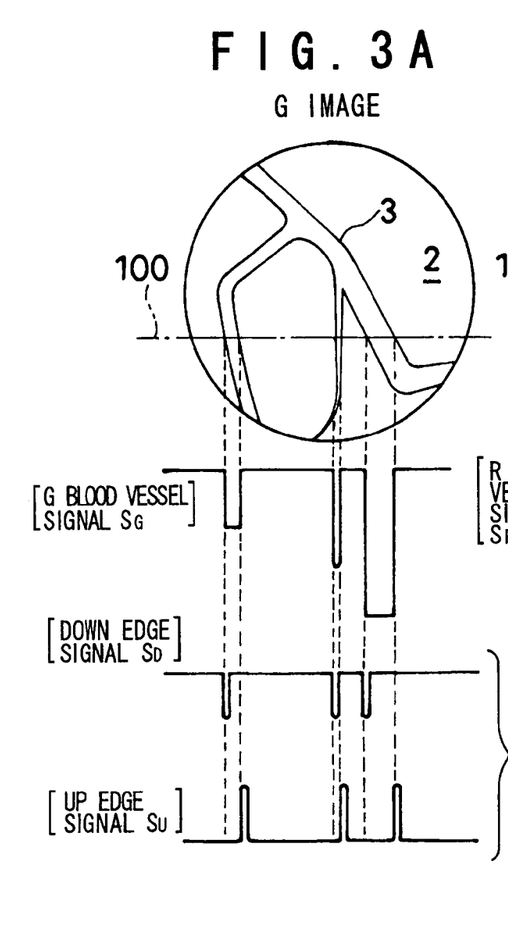
Figure 3B:
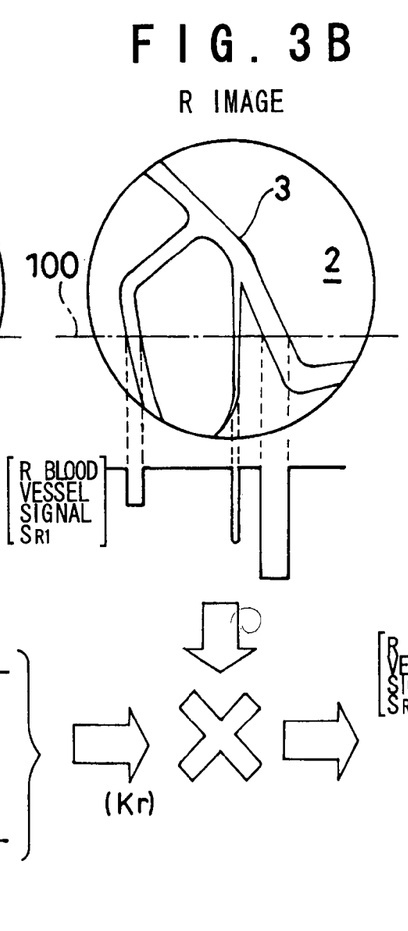
Figure 3C:
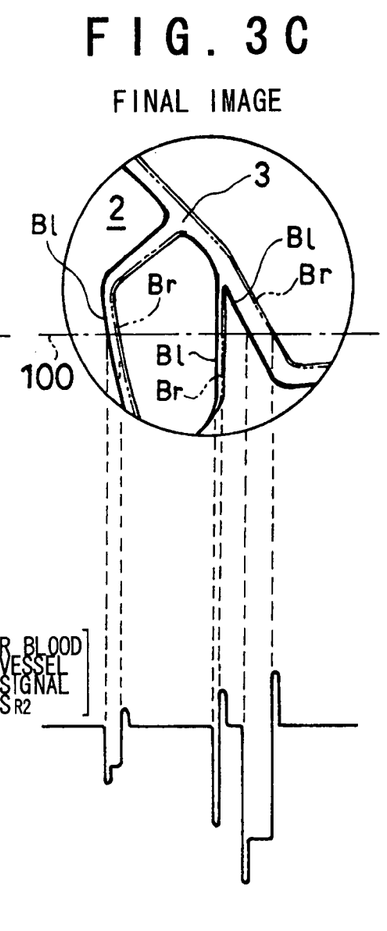

FIG. 3A to FIG. 3C show states of signal processing of this blood vessel highlighting circuit 22 and assuming that a blood vessel signal $S_G$ is obtained on a line 100 of the G signal image as shown in FIG. 3A, the above-described edge detection circuit 30 detects the falling timing of this signal as a down edge signal $S_D$ indicating the down edge section and detects the rising timing of this signal as an up edge signal $S_U$ indicating the up edge section. Then, when the above-described down edge signal $S_D$ is detected, the R coefficient selector 32 selects, for example, 0.6 ($\leq 1$) as the coefficient Kr and when the above-described up edge signal $S_U$ is detected, the R coefficient selector 32 selects, for example, 1.6 ($\geq 1$) as the coefficient Kr and gives this to the multiplier 35A. Likewise, the B coefficient selector 34 also selects a predetermined coefficient Kb (the same coefficient as above or coefficient different from above) in association with the detected down edge signal $S_D$ and up edge signal $S_U$ and supplies these signals to the multiplier 35B.

For example, as shown in FIG. 3B, when a signal $S_{R1}$ of the blood vessel 3 is obtained on the line 100 of the R signal image, a blood vessel signal $S_{R2}$ in the drawing is formed from this blood vessel signal $S_{R1}$ by multiplying the position signals specified by the above-described down edge signal $S_D$ and up edge signal $S_U$ by the coefficient Kr. That is, this signal $S_{R2}$ is a signal whose down edge section is further reduced and whose up edge section is further increased and highlighted and according to this blood vessel signal $S_{R2}$, the final image shows the blood vessel 3 with the blackish left end part B1 (thick line) of the blood vessel and the reddish right end part Br (2-dot dashed line) as shown in FIG. 3C.

The first embodiment has the configuration as shown above and when an object is irradiated with light emitted from the tip of the scope and the image of this object is taken by the CCD 10, then the output signal from this CCD 10 is sampled and amplified by the CDS/AGC 12 and supplied as a digital signal to the DSP 16 through the clamp circuit 14 and A/D converter 15. As described above, this DSP 16 forms a Y signal subjected to various types of image processing and C (color difference) signals of R-Y and B-Y.

Then, when the zoom switch is operated, the electronic zoom circuit 17 electronically magnifies images and also magnifies the blood vessel 3. In the case of an electronic endoscope provided with an optical power scaling mechanism, it is possible to obtain an optically magnified image by driving and controlling the magnification lens of the objective optical system and the electronic zoom circuit 17 can further magnify this optically magnified image. The output of this electronic zoom circuit 17, that is, the Y signal and C signals are converted to R, G and B color signals by the RGB color conversion circuit 21 and these signals are supplied to the blood highlighting circuit 22.

In this blood vessel highlighting circuit 22, a G signal is supplied to the edge detection circuit 30 and the down edge section and up edge section of the blood vessel 3 is detected based on this G signal image. That is, as explained in FIG. 3A, the down edge signal $S_D$ and up edge signal $S_U$ of the G signal blood vessel are extracted and these signals $S_D$ and $S_U$ are supplied to the R coefficient selector 32 and B coefficient selector 34. Then, this R coefficient selector 32 selects a down edge coefficient of, for example, 0.6 for the down edge section and an up edge coefficient of, for example, 1.6 for the up edge section as the coefficient Kr and selects a coefficient of 1.0 for other areas. Then, this coefficient Kr is multiplied on the R signal by the multiplier 35A. As a result, as shown in FIG. 3C, an R blood vessel signal $S_{R2}$ is obtained where the down edge section is further reduced and the up edge section is increased.

On the other hand, the B coefficient selector 34 also selects a down edge coefficient of, for example, 0.8 for the down edge section and an up edge coefficient of, for example, 1.4 for the up edge section as the coefficient Kb and selects a coefficient of 1.0 for other areas. Then, this coefficient Kb is multiplied on the B signal by the multiplier 35B. As a result, a B blood vessel signal similar to $S_{R2}$ in FIG. 3C is obtained.

An image signal output from this blood vessel highlighting circuit 22 is supplied to the monitor through the YC color conversion circuit 23 and character mixing circuit 24, etc. and as shown as the final image in FIG. 3C, both ends are highlighted with the left end part Bl in the blood vessel width direction expressed blackish and the right end section Br expressed reddish on the monitor, thus clearly displaying the blood vessel 3 in optimal contrast. Therefore, even if the blood vessel 3 is in the mucous membrane 2, this makes it easier to observe the blood circulation state and concentration situation of the blood vessel 3 and makes it possible to make a diagnosis of the focus and identify a cancerous tissue, etc. with reference to the blood circulation state, etc. of this blood vessel 3.

As described above, the first embodiment detects the down edge section and up edge section of both ends of the blood vessel in the width direction using, for example, the G signal, gives this down edge section a coefficient smaller than 1 and gives the up edge section a coefficient larger than 1 and multiplies at least the R signal by these coefficients, which highlights both ends of the blood vessel with the left end part expressed blackish and the right end part expressed reddish. This allows blood vessels in tissue such as a mucous membrane to be displayed clearly on the monitor and provides useful information for observation and diagnoses of the object.

The above-described first embodiment detects both ends of the blood vessel based on the G signal image, but can also detect both ends of the blood vessel based on the R signal image, etc. and as shown in FIG. 2, can also supply a brightness (Y) signal output from the electronic zoom circuit 17 (or can also be the DSP 16 if the zoom function is not used) to the edge detection circuit 30 and detect the down edge section and up edge section based on this Y signal. Furthermore, this embodiment multiplies the R signal and B signal by a predetermined coefficient, but can also multiply only the R signal by this coefficient. Furthermore, when edge detection is performed by the Y signal, coefficient calculations can also be performed on the color difference (C) signals.

Second Embodiment

Figure 4:
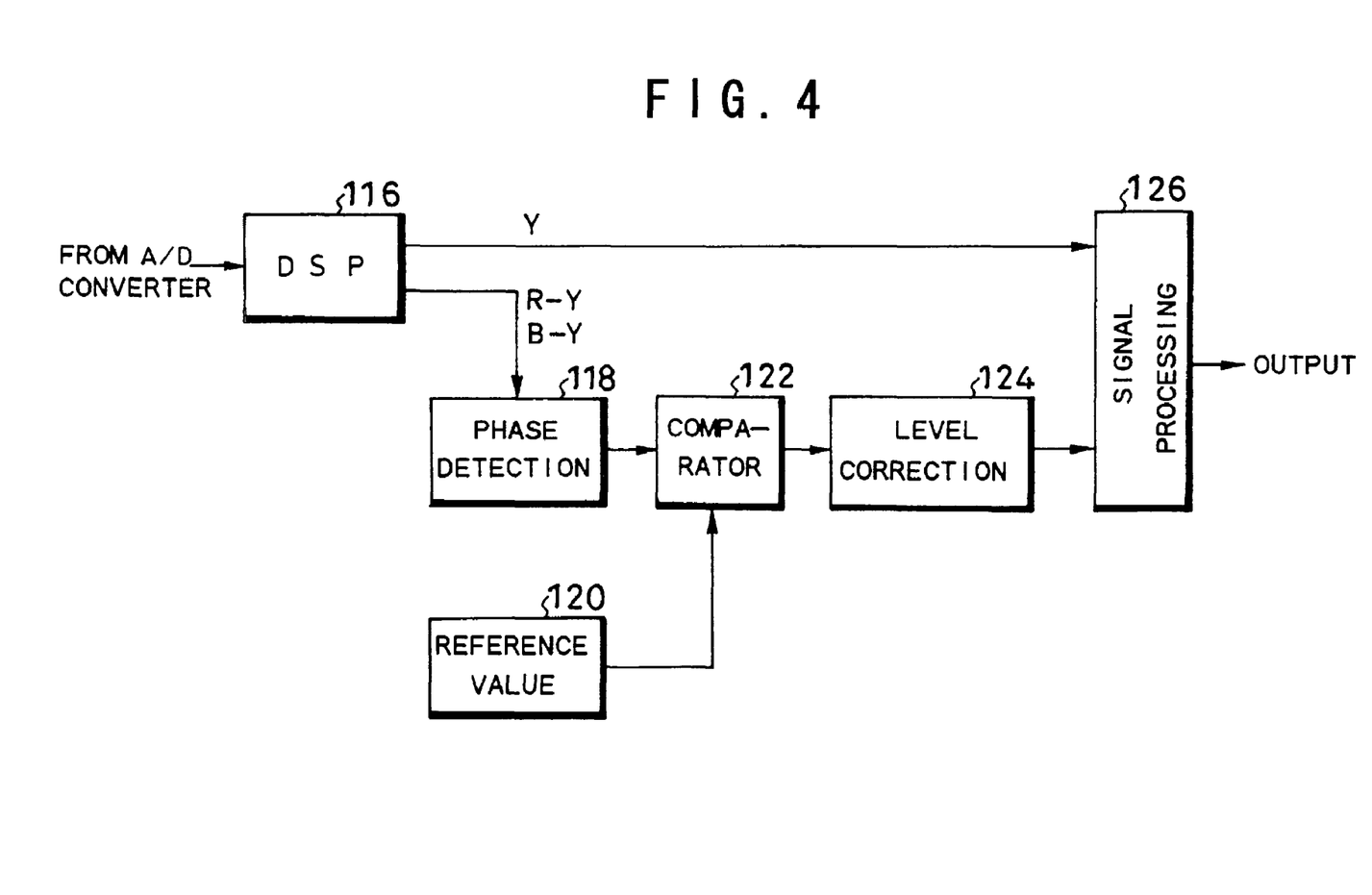
FIG. 4 is a block diagram showing a main configuration of an electronic endoscope according to a second embodiment.

FIG. 4 shows a main configuration of an electronic endoscope according to a second embodiment and the rest of the configuration except that shown in this FIG. 4 is the same as that in FIG. 1. A video signal is supplied to a DSP 116 in FIG. 4 through an A/D converter 15. This DSP 116 forms a Y (brightness) signal and forms color difference signals of R (red)-Y and B (blue)-Y by applying color conversion operations to signals obtained through various color filters of Mg, G, Cy and Ye. Then, the second embodiment performs processing to clearly display blood vessels as specific objects using these R-Y signal and B-Y signal.

That is, this embodiment is provided with a phase detection circuit 118 that inputs the above R-Y signal and B-Y signal and detects the phases of these signals, a reference value setting circuit 120 that outputs $\theta_1$ which is the phase of the blood vessel color (to be exact, $\theta_1$ with tolerance of ±α) as a reference value, a comparator 122 that compares the phase detected by the above phase detection circuit 118 with the above reference value $\theta_1$ and extracts the signal of phase $\theta_1$ of the blood vessel color and a level correction (amplification) circuit 124 that amplifies the signal level of the blood color extracted by this comparator 122 up to a predetermined level.

Figure 5:
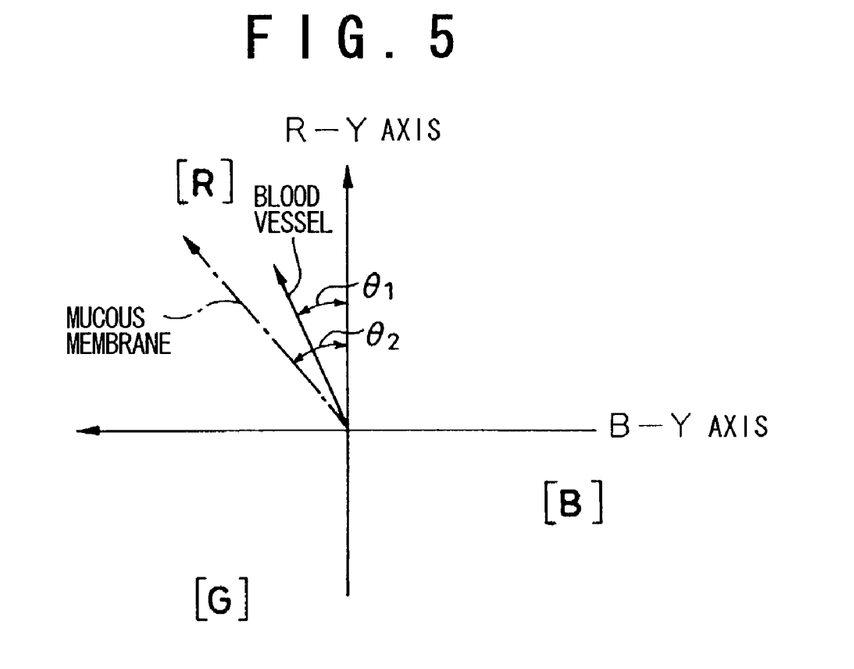
FIG. 5 is a graph showing phases of a blood vessel and a mucous membrane according to the second embodiment on a two-dimensional coordinate system.

FIG. 5 shows a phase relationship between a blood vessel and mucous membrane and when R-Y is set on the vertical axis and B-Y is set on the horizontal axis on a two-dimensional coordinate system, R (red) is located in the second quadrant, G (green) is located in the third quadrant and B (blue) is located in the fourth quadrant. Then, as shown in the drawing, the color of the blood vessel exists at the position of the phase of $\theta_1$ from the R-Y axis, the color of the mucous membrane exists at the position of the phase of $\theta_2$. Therefore, if the signal of phase $\theta_1$ is extracted by the above phase detection circuit 118 and comparator 122 (specific object extraction circuit), it is possible to extract the color signal of the blood vessel and amplify only this color signal using the above level correction circuit 124. Signals other than that of this blood vessel are output as they are.

Furthermore, the above level correction circuit 124 is followed by a signal processing circuit 126 and this signal processing circuit 126 performs various kinds of processing for monitor output based on the color difference signals (R-Y signal, B-Y signal) with the blood vessel color levels corrected and the brightness signal output from the above DSP 116. By the way, the above-described phase detection circuit 118, comparator 122 and level correction circuit 124 can be constructed incorporated in a microcontroller.

The second embodiment is configured as shown above and the output signal from the CCD 10 in FIG. 1 is sampled and amplified by the CDS/AGC 12 and supplied as a digital signal to the DSP 116 through the A/D converter 15. As described above, this DSP 116 in FIG. 4 forms a Y signal subjected to various types of image processing and R-Y signal and B-Y signal which are color difference signals and these R-Y signal and B-Y signal are supplied to the phase detection circuit 118, comparator 122 and level correction circuit 124.

Figure 7:
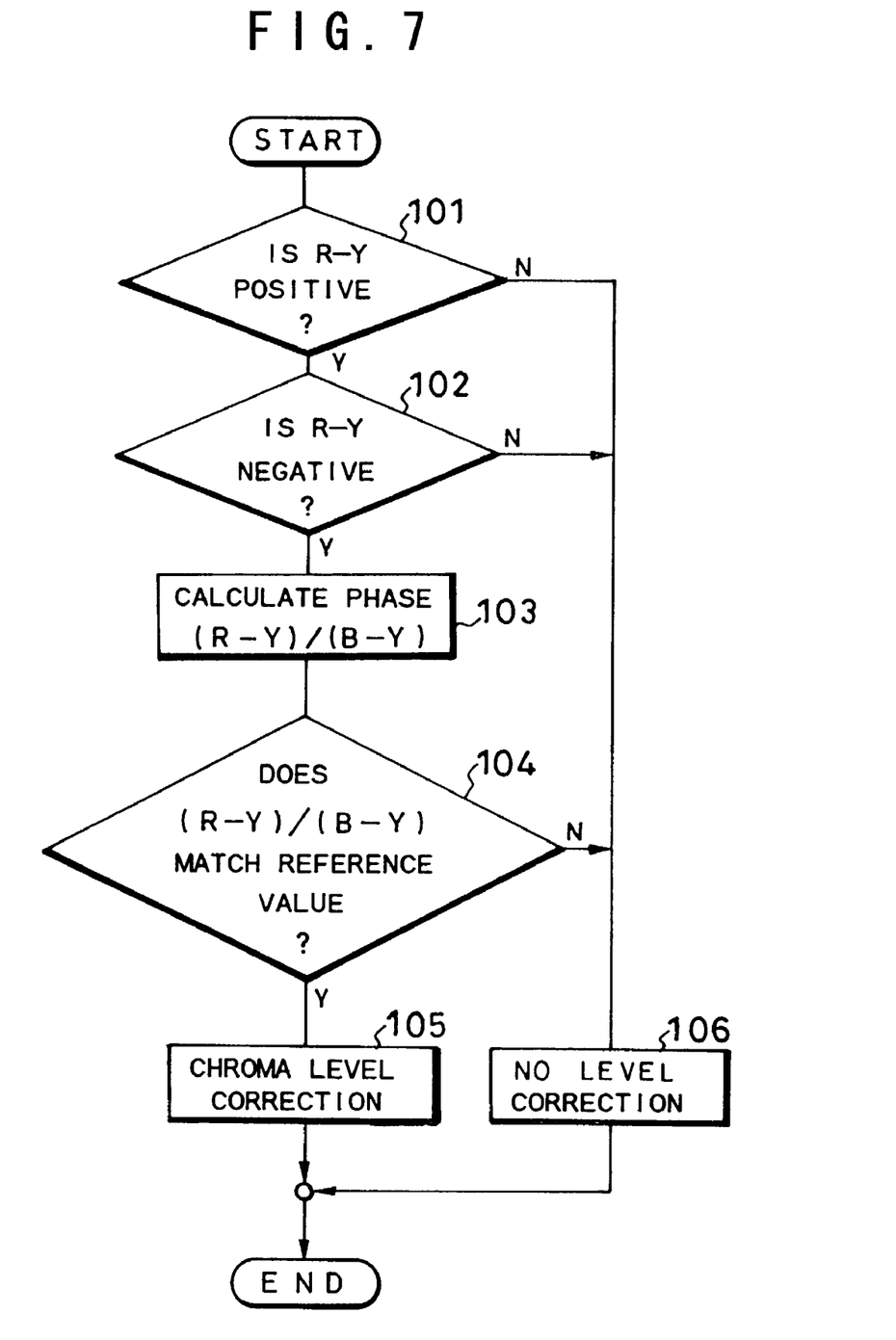
FIG. 7 is a flow chart showing basic operations of a phase detection circuit, a comparator and the level correction circuit according to the second embodiment.

FIG. 7 shows basic operations of the above phase detection circuit 118, comparator 122 and level correction circuit 124, and as shown in step 101, the above phase detection circuit 118 decides whether the R-Y signal is positive or not, decides in next step 102 whether the B-Y signal is negative or not, and when both are Y (YES), that is, when both signals exist in the second quadrant in FIG. 5, the phase of the color difference signal is calculated by (R-Y)/(B-Y) in step 103. Then, as shown in step 104, the comparator 122 compares the detected phase "(R-Y)/(B-Y)" with the reference value $\theta_1$ indicating the blood vessel color to see if the two values match or not and extracts a color difference signal that matches this reference value $\theta_1$, or to be exact, a signal whose phase ranges from $\theta_1 - \alpha$ to $\theta_1 + \alpha$.

Figure 6:
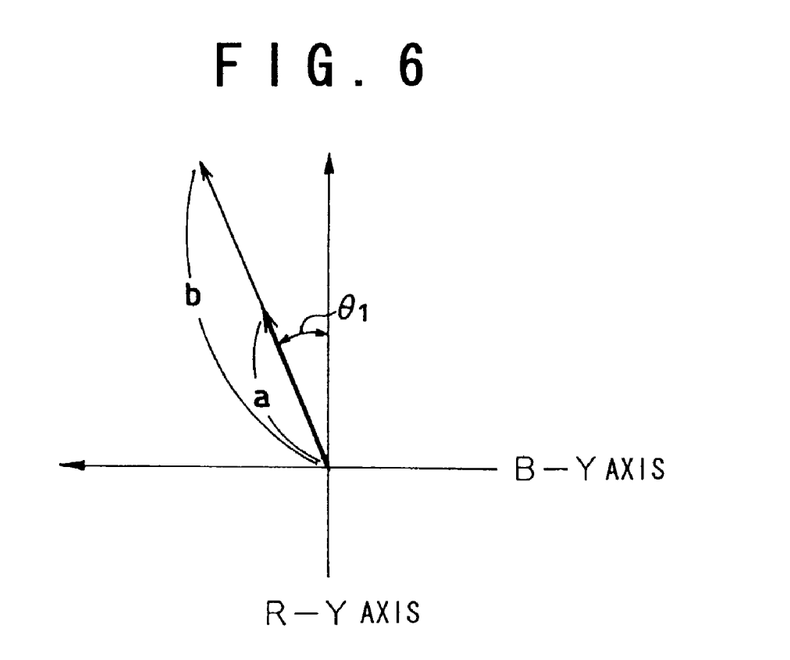
FIG. 6 is a graph showing an example of a blood vessel color amplified by a level correction circuit according to the second embodiment on the coordinate system.

Then, the level correction circuit 124 corrects the chroma level shown in step 105 and amplifies the level of a color difference signal that matches the above reference value $\theta_1$ a predetermined number of times. FIG. 6 shows a state in which the level of the blood vessel color is amplified and, for example, if the level of the color difference signal that matches the reference value $\theta_1$ is "a" and the amplification factor is ×2 (double), then a color difference signal indicating the blood vessel at level b ($b=2a$) is obtained from the level correction circuit 124. When the results in steps 101, 102 and 104 are N (NO), level correction is not performed as shown in step 106.

According to the second embodiment, it is possible to display the magnified image 1 as shown in FIG. 8 on the monitor by driving the power scaling lens built in the objective optical system as described above and the processing related to the above blood vessel allows the blood vessel (capillary blood vessel) 3 to be displayed clearly as the above magnified image 1 in optimum contrast to the membrane 2, which consequently makes it possible to clearly observe the blood circulation state and concentration situation of the blood vessel 3, clearly observe and identify the areas of focuses such as cancerous tissue.

The second embodiment treats blood vessels as specific objects, but can also treat cancerous tissue itself and tissue with different degrees of inflammation and symptoms as specific objects or can select tissue which does not correspond to a specific one but differs from blood vessels in the level of redness as a specific object, and by extracting color difference signals using phases of these specific objects as reference values, it is possible to increase the contrast of the specific objects in relation with other tissues such as mucous membranes.

Furthermore, the above level correction circuit 124 amplifies the signal level indicating blood vessels. On the contrary, it is also possible to make clear blood vessels by reducing the signal level other than those of blood vessels. Furthermore, the above embodiment has used the R-Y signal and B-Y signal as color difference signals, but it is also possible to use other color difference signals such as modified R-Y signal or B-Y signal.

As explained above, the second embodiment has made it possible to extract signals of phases of blood vessel colors on the coordinate system in which the R-Y signal is set on the vertical axis and B-Y signal is set on the horizontal axis, increase/decrease the level of these signals and adjust chroma of specific object colors, which allows specific objects such as blood vessels to be displayed clearly on the monitor in high contrast to other tissues such as mucous membrane. Then, combining the blood vessel highlighting processes of both the second and first embodiments above can produce synergetic effects.

What is claimed is:

1. An electronic endoscope comprising:
   a color signal processing circuit that forms predetermined signals for color displays based on signals captured by an image pickup element;
   a blood vessel edge detection circuit that inputs predetermined signals output from said color signal processing circuit and detects both ends of a blood vessel in a width direction;
   a multiplier that multiplies each of both ends of the blood vessel detected by said blood vessel edge detection circuit by a predetermined coefficient,
   wherein a blood vessel highlighting circuit is formed of said blood vessel edge detection circuit and said multiplier; and
   wherein said blood vessel highlighting circuit detects a down edge section and an up edge section at both ends of the blood vessel in the width direction using said blood vessel edge detection circuit, multiplies said down edge section by a coefficient smaller than 1 and multiplies said up edge section by a coefficient larger than 1.

2. The electronic endoscope according to claim 1, wherein said color signal processing circuit forms red, green and blue color signals, said blood vessel highlighting circuit detects both ends of the blood vessel by using said green signal and multiplies at least a red signal by the coefficients corresponding to both ends of the blood vessel.

3. The electronic endoscope according to claim 1, wherein said color signal processing circuit forms a brightness signal, said blood vessel highlighting circuit detects both ends of the blood vessel by using the brightness signal and multiplies color difference signals or red, green and blue color signals by this coefficients corresponding to both ends of the blood vessel.

* * * * *